US009443708B2

(12) United States Patent
Farmer, III et al.

(10) Patent No.: US 9,443,708 B2
(45) Date of Patent: Sep. 13, 2016

(54) ION IMPLANTATION SYSTEM AND PROCESS FOR ULTRASENSITIVE DETERMINATION OF TARGET ISOTOPES

(71) Applicants: Orville T. Farmer, III, Kennewick, WA (US); Martin Liezers, Richland, WA (US)

(72) Inventors: Orville T. Farmer, III, Kennewick, WA (US); Martin Liezers, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 135 days.

(21) Appl. No.: 14/482,332

(22) Filed: Sep. 10, 2014

(65) Prior Publication Data

US 2016/0071713 A1    Mar. 10, 2016

(51) Int. Cl.
*H01J 49/04* (2006.01)
*H01J 37/317* (2006.01)
*G01N 1/40* (2006.01)
*H01J 37/05* (2006.01)
*G01N 1/44* (2006.01)
*G01N 1/38* (2006.01)

(52) U.S. Cl.
CPC .......... *H01J 49/0459* (2013.01); *H01J 49/04* (2013.01); *G01N 1/405* (2013.01); *G01N 1/44* (2013.01); *G01N 2001/388* (2013.01); *H01J 37/05* (2013.01); *H01J 37/3171* (2013.01)

(58) Field of Classification Search
USPC ...................................................... 250/492.3
See application file for complete search history.

(56) References Cited

U.S. PATENT DOCUMENTS

| 5,751,002 | A | 5/1998 | Ogata et al. | |
| 6,670,624 | B1 | 12/2003 | Adams et al. | |
| 6,835,927 | B2 * | 12/2004 | Becker | H01J 49/0036 250/281 |
| 6,989,528 | B2 * | 1/2006 | Schultz | H01J 49/0031 250/281 |
| 7,851,773 | B2 | 12/2010 | Glavish et al. | |
| 8,110,820 | B2 | 2/2012 | Glavish et al. | |
| 8,354,654 | B2 | 1/2013 | Chen | |
| 8,383,420 | B2 * | 2/2013 | Kingston | G01N 1/405 435/7.92 |
| 2009/0206270 | A1 | 8/2009 | Glayish et al. | |

OTHER PUBLICATIONS

International Search Report/Written Opinion for International Application No. PCT/US2015/033015, International Filing Date May 28, 2015, Date of Mailing Oct. 7, 2015.
Dion, M. P., et al., Improving alpha spectrometry energy resolution by ion implantation with ICP-MS, Journal of Radioanalytical and Nuclear Chemistry, 303, 2015, 877-884.
Becker, J. S., et al., Investigation of Cu-, Zn- and Fe-containing human brain proteins using isotopic-enriched tracers by LA-ICP-MS and MALDI-FT/ICR-MS, International Journal of Mass Spectrometry, 242, 2005, 135-144.
Anonymous, Isotope dilution, Retrieved from the Internet: URL:https://en.wikipedia.org/w/index.php?title=Isotope_dilution &oldid=618935782m Jul. 29, 2014.
(Continued)

*Primary Examiner* — Phillip A Johnston
(74) *Attorney, Agent, or Firm* — James D. Matheson

(57) ABSTRACT

A system and process are disclosed for ultrasensitive determination of target isotopes of analytical interest in a sample. Target isotopes may be implanted in an implant area on a high-purity substrate to pre-concentrate the target isotopes free of contaminants. A known quantity of a tracer isotope may also be implanted. Target isotopes and tracer isotopes may be determined in a mass spectrometer. The present invention provides ultrasensitive determination of target isotopes in the sample.

19 Claims, 5 Drawing Sheets

(56) References Cited

OTHER PUBLICATIONS

Liezers, M., et al., The production of ultra-high purity single isotopes or tailored isotope mixtures by ICP-MS.

Vogl, J., et al., Isotope Dilution Mass Spectrometry—A Primary Method of Measurement and Its Role for RM Certification, MAPAN—Journal of Metrology Society of India, vol. 25, No. 3, 2010, 135-164.

* cited by examiner

ION IMPLANTATION SYSTEM AND PROCESS FOR ULTRASENSITIVE DETERMINATION OF TARGET ISOTOPES

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The present invention relates generally to analytical instruments for determination of isotopes. More particularly, the present invention relates to an ion implantation system and process for pre-concentration of target isotopes for ultrasensitive elemental analysis.

BACKGROUND OF THE INVENTION

A need exists to improve elemental detection limits for production of ultra-pure materials used in various industries including, e.g., the semiconductor industry and nuclear industry, and in such fields as, e.g., geochemistry and biochemistry. Various instruments and methods are currently used for determination of most elements in the periodic table such as Inductively Coupled Plasma Mass Spectrometry (ICP-MS) that report theoretical detection limits of $<10^6$ atoms/mL. However, in practice, theoretical detection limits are rarely achieved due to elemental contamination of samples and process blanks that occurs during preparation for instrumental analysis. Common sources of contamination include: contaminants present in chemicals used to dissolve samples, contaminants leached from walls of the container, and contaminants introduced into samples from air borne particulates. The terms "contaminant" or "contamination" as used herein means an unwanted or undesirable minor constituent introduced into a sample material or a process blank undergoing analysis that interferes with quantitation of a target isotope or a background measurement. Contaminants introduced into samples and process blanks during sample preparation can easily exceed impurities present in the original sample since concentration of original impurities often drops to trace and ultra-trace levels in ultra-pure samples due to dilution. Thus, accurate measurement of target isotopes in an original sample can often become impossible because of contamination-generated backgrounds, not because of sensitivity limitations of the analytical technique being used. Consequently, detection limits for most elements lie only in the range from about $10^9$ atoms/mL (1 ppt) to about $10^{12}$ (1 ppb). Accordingly, new systems and processes are needed that minimize contamination thereby providing reliable, ultrasensitive determination of target isotopes in high and ultra-high purity materials. The present invention addresses these needs.

SUMMARY OF THE INVENTION

The present invention includes a new mass-selective isotope implantation system and process for ultrasensitive determination of trace level isotopes in a sample. The system may include an ablation device configured to ablate a sample containing a target isotope of interest. The term "target isotope" means an element of analytical importance in a sample with an unknown concentration such as a trace level contaminant. For solid samples, the ablation device may yield an ablation plume containing solid particles of a selected size. The system may also include a high-temperature plasma device that atomizes ablated sample particles at a temperature at or above about 4000 Kelvin and forms a plasma plume containing ions of the target isotopes. The system may also include a mass-selective spectrometer that mass selects target isotopes at selected masses and filters the target isotopes from bulk sample matrix components that can normally interfere with the determination of the isotope of interest, particularly at trace levels. Filtered target isotopes may be implanted in one or more implant areas of a selected size on the surface of a high-purity substrate free of surface contaminants. The system may also implant tracer isotopes onto the same high-purity substrate or a different high-purity substrate. The term "tracer isotope" means an isotope of the same element as the target isotope or a different element than the target isotope that is implanted onto the substrate before or after the target isotopes that assists in the determination of the concentration of the target isotope of interest. For example, tracer isotopes form an isotopic dilution standard with the target isotopes on the substrate in the solid phase that permits ultrasensitive determination of the concentration of the target isotopes.

In some embodiments, the system may include an ablation device with an ablation laser configured to deliver an ablation beam of a selected beam width less than or equal to about 1 mm that ablates the solid sample into solid particles of a selected size. Ablation sources may deliver an ablation beam with a power density selected between about 0.1 J/cm² to about 20 J/cm².

In some embodiments, samples may be ablated with a glow discharge source that releases target isotopes in a controlled gas atmosphere that may be implanted on a high-purity substrate in preparation for analysis.

In some embodiments, the ablation device may include a laser ablation source that delivers an ablation beam with a selected pulse width. In some embodiments, pulse widths may be femtosecond pulse widths. In some embodiments, pulse widths may be nanosecond pulse widths. In some embodiments, pulse widths may be selected from about 1 femtosecond to about 20 nanoseconds.

In some embodiments, the ablation source may be an electrical spark ablation source. Laser ablation and spark ablation sources are preferred as they require little or no sample preparation so contamination stemming from acid dissolution of solid samples in containers is avoided.

The present invention also includes a high-purity substrate with at least one target isotope and at least one tracer isotope implanted in an implant area of a selected size on the substrate. The target isotope and tracer isotope form an isotope dilution standard on the substrate in the solid phase that provides for ultrasensitive determination of the target isotope. In some embodiments, the substrate on which the target isotopes are implanted may be comprised of a tracer isotope. Isotopes implanted on the substrate are free of bulk sample matrix components and solution contaminants.

High-purity substrates suitable for use may include, but are not limited to, e.g., metals, metal foils, semiconductors, silica, plastics, and combinations of these various materials.

Implanted tracer isotopes and target isotopes when ablated from the substrate may be released to a mass spectrometer that permits the isotope dilution ratio of the isotopes to be determined for ultrasensitive determination of the target isotope.

In some embodiments, the substrate may be polarized with a bias voltage that facilitates implantation of target isotopes and tracer isotopes onto the surface of the substrate.

The present invention also includes a method for ultrasensitive determination of target isotopes of interest in various samples. The method may include implanting the target isotope onto a selected implant area of a selected size on the surface of a high-purity substrate to pre-concentrate the target isotope. The implanted target isotope is substantially free of sample matrix components and contaminants which permit ultrasensitive determination of the target isotope. A known quantity of a selected tracer isotope may be implanted on the same or different implant area to form an isotope dilution standard with the target isotope on the surface of the high-purity substrate in the solid phase. The implant area on the substrate may be ablated to release the target isotope and the tracer isotope into a mass spectrometer where the target isotope may be determined.

The method may alternatively include implanting the target isotope on a high-purity substrate comprised of the selected tracer isotope to form an isotope dilution standard on the surface of the substrate in the solid phase.

Determining the concentration of the target isotope may include determining the isotope dilution ratio of the target isotope and the tracer isotope. The concentration of the target isotope may then be calculated from the ion detector responses for the known quantity of tracer isotopes and the target isotopes.

The tracer isotope may be a surrogate isotope of an element with a mass that is identical to or adjacent to that of the target isotope. The tracer isotope may be another isotope of the target element of interest.

The sample containing target isotopes of analytical interest may be ablated in an ablation device. Samples may include, but are not limited to, e.g., solids, gases, liquids. Solids may include, but are not limited to, e.g., metals, ceramics, composites, aggregates, glasses, plastics, semiconductors, minerals, and combinations of these various materials. Target isotopes in these samples may include any elements from the periodic table. In various embodiments, target isotopes may be selected from hydrogen (H) to curium (Cm). In some embodiments, target isotopes may include combinations of various elements.

The sample may be ablated to form an ablation plume containing the target isotopes released from the sample. In some embodiments, the ablated sample may include particles of a size below about 10 µm or smaller. Particles may be swept in a sweep gas including, but not limited to, e.g., argon (Ar), helium (He), nitrogen ($N_2$), oxygen ($O_2$), air, and combinations of these gases from the ablation device to a high-temperature plasma device. Gas pressures may be at atmospheric pressure or a greater pressure.

The implant area containing both the pre-concentrated target isotope and the tracer isotope may then be ablated. The isotope dilution ratio of the target isotope and the tracer isotope may be determined in a mass spectrometer.

Target isotopes received from the laser ablation device may be ionized (atomized) in a high-temperature plasma device at a temperature above 4000 K to form ions of the target isotopes prior to implanting the target isotopes on the surface of the substrate. In some embodiments, atomization of the target isotopes may be performed at a temperature between about 5,000 Kelvin to about 10,000 Kelvin.

The high-temperature plasma may be generated from the sweep gas or other support gases that include gas pressures greater than or equal to about 0.5 atmospheres.

High-temperature plasma devices may include, but are not limited to, e.g., inductively coupled plasma devices, microwave devices, AC-arc plasma devices, DC-arc plasma devices, and combinations of these devices. In some embodiments, the high-temperature plasma device may be a inductively coupled plasma (ICP) device that is configured to receive the ablation plume containing pre-concentrated target isotopes an tracer isotopes released from the substrate in the ablation device. The high-temperature plasma may ionize the pre-concentrated target isotopes and tracer isotopes released from the substrate by the ablation device and deliver the ablated isotopes to the mass spectrometer for determination of the isotopic dilution ratio of both the target isotopes and the tracer isotopes at an ultrasensitive detection limit.

Target isotopes of interest may be filtered from the bulk matrix component ions introduced from the high-temperature plasma device into the mass-selective spectrometer. Target isotopes may be mass-selected at selected masses prior to implanting the target isotopes on the surface of a high-purity substrate. The high-purity substrate on which the target isotopes are implanted may replace a mass detector in the mass-selective spectrometer.

Target isotopes may be implanted in a selected implant area on the surface of the high-purity substrate free of bulk matrix components and free of solution contaminants conventionally introduced by wet chemistry methods from such sources as, e.g., liquid dissolution reagents and/or leaching of sample containers. Removal of bulk matrix components and solution contaminants minimizes or eliminates backgrounds that permit ultrasensitive determination of target isotopes of interest. The present invention also directly by-passes need for wet chemistry separation techniques employed conventionally when trace target isotopes of interest cannot be measured due to the presence of bulk sample matrix components that generate large background interferences.

Implantation of both a known quantity of a tracer isotope and the isotope of analytical interest from the sample forms an Isotopic Dilution Analysis (IDA) standard on the surface of the substrate in the solid phase. Isotopic Dilution Analysis (IDA) is conventionally performed only with wet chemistry methods which introduce contamination problems described previously. Thus, Isotopic Dilution Analysis (IDA) in the solid phase represents a new development in the art. Ablation of the target isotope and the tracer isotope then permits determination of the isotope dilution ratio of both isotopes in a mass spectrometer. The detector response for the tracer isotope and the target isotope permit ultrasensitive determination of the concentration of the target isotope in the sample.

Implantation of the present invention may be performed with any suitable mass spectrometry based system. Mass spectrometry systems include, but are not limited to, e.g., Glow Discharge Mass Spectrometry (GD-MS); Secondary Ion Mass Spectrometry (SIMS); Inductively Coupled Plasma Mass Spectrometry (ICP-MS).

In some embodiments, a known quantity of a selected tracer isotope may be implanted on the surface of a substrate.

In some embodiments, a known quantity of a tracer isotope that is a different isotope of the target isotope may be implanted on the surface of the substrate.

In some embodiments, a known quantity of a selected tracer isotope may be implanted with the target isotope in an implant area on the surface of the high-purity substrate to form an isotope dilution standard in the solid phase.

The implant area containing both the pre-concentrated target isotope and the tracer isotope may then be ablated. The isotopic dilution ratio of both isotopes may be determined in any suitable mass spectrometer. Mass spectrometry systems include, but are not limited to, e.g., Glow Discharge Mass Spectrometry (GD-MS); Secondary Ion Mass Spectrometry (SIMS); Inductively Coupled Plasma Mass Spectrometry (ICP-MS).

In some embodiments, the substrate on which the target isotopes are implanted may be comprised of the selected tracer isotope.

The high-purity substrate for implantation may be positioned in a mass spectrometer in place of a conventional mass spectrometry detector.

A known quantity of a selected tracer isotope of the same or different elements may also be implanted on the same or different implant areas to form an isotope dilution standard in the solid phase on the surface of the substrate.

The tracer isotope may be implanted in the implant area on the surface of the substrate before or after the target isotope.

Implant areas on the substrate may include a cross-sectional area of less than a square millimeter ($<<1$ $mm^2$) to an area of about a square micrometer (1 $\mu m^2$) which pre-concentrates target isotopes of analytical interest.

The present invention effectively pre-concentrates target isotopes including radioactive and non-radioactive isotopes and minor impurity isotopes of analytical importance onto a substrate in a mass spectrometer. The mass spectrometer effectively filters and removes primary or bulk matrix components of a sample material permitting trace level isotopes of analytical interest to be determined.

The target isotope may be pre-concentrated by a factor of at least about 10 times or greater on the surface of the substrate.

The same or different ablation device may be coupled to a high-temperature plasma device and to a mass spectrometer (MS) for determination of the target isotopes and the tracer isotopes. The ablation device may be configured to receive the high-purity substrate with the implanted target isotopes and tracer isotopes. The ablation device may ablate the implant area on the surface of the substrate containing the implanted and pre-concentrated target isotopes and tracer isotopes to release the target isotopes and tracer isotopes from the surface of the substrate for analysis.

Analyzing the target isotopes may include ablating one or more implant areas on the surface of the high-purity substrate containing implanted target isotopes and tracer isotopes with an ablation device in a selected ablation time. The ablated target isotopes and tracer isotopes may be delivered to a mass analyzer for determination of both isotopes.

In some embodiments, ablation of the implant areas may include raster scanning the implant areas on the substrate with an ablation laser that ablates and releases the target isotopes and the tracer isotopes in a selected time to a mass spectrometer. The mass spectrometer determines the isotope dilution ratio for both the pre-concentrated target isotopes and the tracer isotopes, which yields strong ion current signals that allows ultrasensitive determination of the target isotopes of interest.

In some embodiments, a raster scan may be employed to ablate the implant area on the surface of the substrate in a selected ablation pattern and selected ablation time to release the target isotopes and tracer isotopes.

In some embodiments, the ablation laser may be set to ablate implant areas on the surface of the substrate containing target isotopes and tracer isotopes in a raster scan that is performed in a selected ablation time. The raster scan may account for a maximum area of about 10% of the surface.

In some embodiments, the raster scan may include an ablation time less than or equal to about 80 seconds; or less than or equal to about 60 seconds; or less than or equal to about 50 seconds; or less than or equal to about 40 seconds; or less than or equal to about 30 seconds; or less than or equal to about 20 seconds; or less than or equal to about 10 seconds. No limitations are intended.

Analysis of target isotopes and tracer isotopes implanted on the substrate may include ablating one or more implant areas on the surface of the substrate containing the implanted target isotopes and a known quantity of implanted tracer isotopes. Tracer isotopes may be different isotopes of the same target element, or a different element than the target isotope if the target element is mono-isotopic. An ion current signal for the tracer isotopes and the target isotopes may be obtained in a mass spectrometer. The ion signal corresponding to the known quantity of tracer isotopes may then provide ultrasensitive determination of the concentrations of the target isotopes in the original sample.

In some embodiments, the present invention determines the concentration of target isotopes in a mass spectrometer at a detection limit of at least about $10^8$ atoms per $cm^2$ or lower.

In some embodiments, the present invention determines the concentration of target isotopes in a mass spectrometer at a detection limit of at least about $10^7$ atoms per $cm^2$ (2 ppt) or lower.

The present invention finds application in manufacturing of ultra-high purity materials (e.g., semiconductors) or where ultrasensitive detection of target isotopes at below current process blank levels is desired, including, e.g., in nuclear detection, geochemistry, and biochemistry applications.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DETAILED DESCRIPTION

Figure 1:
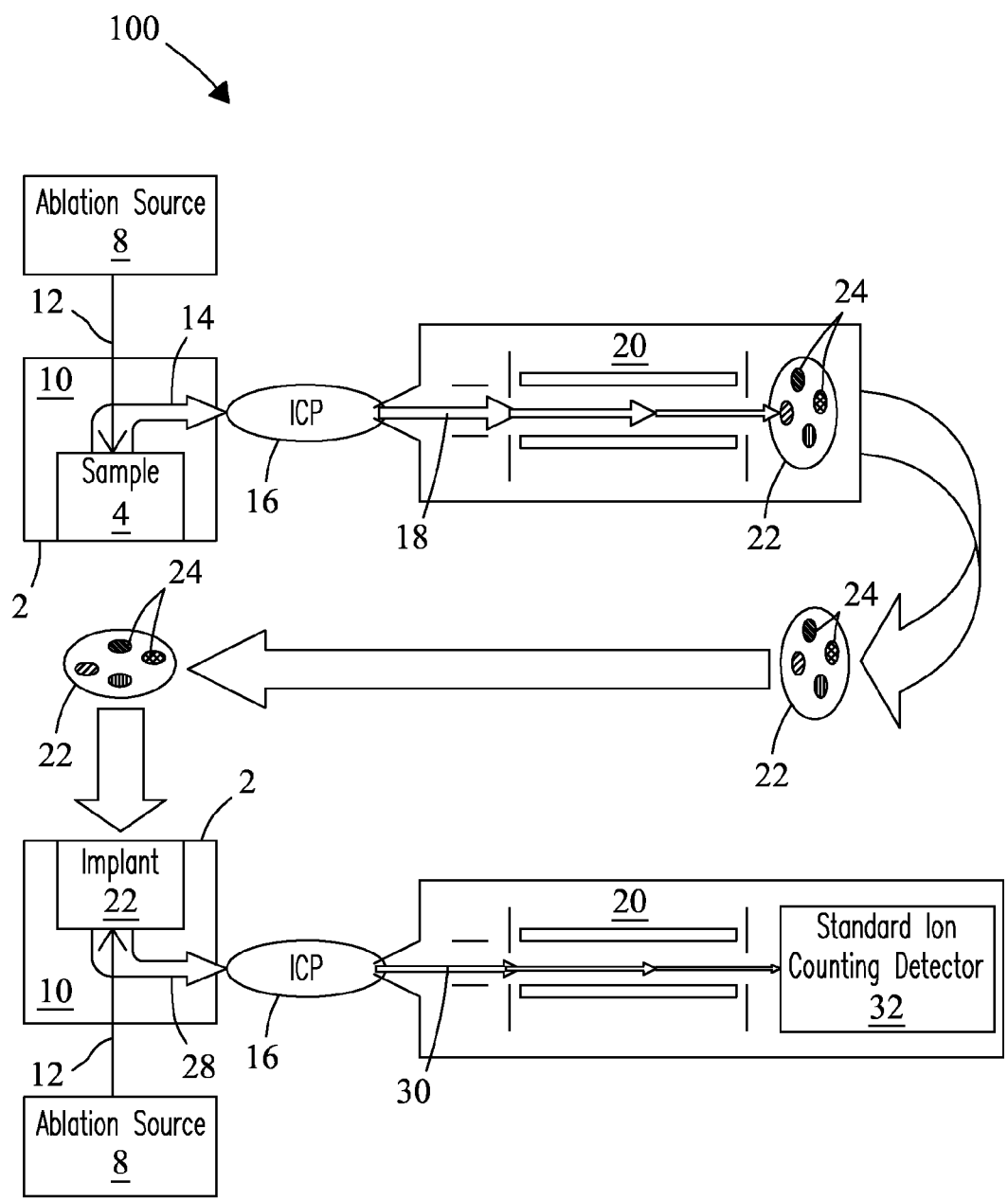
FIG. 1 shows a system for implantation of single or multiple isotopes at selected masses on a substrate for ultrasensitive analysis of target isotopes.

The present invention includes a system and process for ultrasensitive determination of target isotopes. In the following description, embodiments of the present invention are shown and described by way of illustration of the best mode contemplated for carrying out the invention. It will be clear that the invention is susceptible of various modifications and alternative constructions. The present invention covers all modifications, alternative constructions, and equivalents falling within the spirit and scope of the invention as defined in the claims. Therefore the description should be seen as illustrative and not limiting. While the present invention is described herein in reference to LA-ICP-MS, the invention is not intended to be limited thereto, as detailed further herein. FIG. 1 illustrates an exemplary system 100 of the present invention for ultrasensitive determination of target isotopes in a sample. System 100 may include an ablation device 2 for ablation of samples 4 containing target isotopes of analytical interest or trace level impurities of analytical importance. Samples are not limited. Samples may include, but are not limited to, e.g., any solid or liquid material that can be ablated or nebulized including, but not limited to, e.g., metals, semiconductors, ceramics, glasses, plastics, other solids, liquids, and combinations of these various sample materials.

In some embodiments, ablation devices may include, but are not limited to, e.g., laser ablation devices; electrical-spark ablation devices (e.g., RF, AC, and DC electrical-spark ablation devices); glow-discharge devices (e.g., RF, AC, DC, and pulsed glow-discharge devices); high-energy atom bombardment devices; and high-energy electron bombardment devices [e.g., Secondary Ion Mass Spectrometry (SIMS) devices] configured to sputter atoms and/or ions from the surface of a sample. Laser ablation devices may include pulse laser devices including, but not limited to, e.g., Quantum Cascade (QC) lasers, Distributed Feedback (DFB) lasers, Inductively Coupled (IC) lasers, External Cavity (EC) QC lasers, diode lasers, and combinations of these lasers. In other embodiments, ablation devices may include thermal ablation devices, radio frequency (RF) ablation devices, bipolar RF ablation devices, RF clamp ablation devices, RF linear ablation devices, microwave ablation devices, ultrasound ablation devices, radiation ablation devices, electrical ablation devices, and combinations of these ablation devices.

Ablation device 2 may include an ablation source 8 such as a pulsed UV ablation laser 8 that ablates samples 4. In some embodiments, solid samples may be ablated into sample particles of a selected size. Particle sizes are not limited. In some embodiments, sample particles may be of a micrometer size on average. In some embodiments, sample particles may include a size below about 10 nm on average. In some embodiments, sample particles may be at or below about 1 nanometer in size. No limitations are intended.

Ablation laser 8 may deliver a pulsed ablation beam 12 of a selected beam width. Pulse widths of ablation source 8 are not limited. In various embodiments, pulse widths of pulse ablation sources may range from about femtosecond pulse widths to about microsecond pulse widths. However, no limitations are intended. For example, in some embodiments, ablation beam 12 may include a beam width less than or equal to about 780 micrometers (μm). Ablation laser 8 may deliver pulsed ablation beams 12 for selected time intervals or periods, e.g., from nanoseconds to femtoseconds. Ablation beam 12 may include selected wavelengths, e.g., from infra-red to vacuum ultraviolet. Wavelengths are selected that generate a sufficiently high power density to provide explosive heating that ablate samples 4.

Ablated sample particles may be delivered in an ablation plume 14, e.g., in a sweep gas from ablation chamber 10 into a high-temperature plasma device 16. High-temperature plasma devices suitable for use include, but are not limited to, e.g., Inductively Coupled Plasma (ICP) devices, glow-discharge plasma devices, high pressure glow discharge devices, hollow cathode discharge devices, spray discharge devices, corona discharge devices, electric arc discharge devices, vacuum arc devices, thermal plasma devices, strong electromagnetic field plasma devices, laser plasma devices, microwave plasma devices, complex plasma devices, non-neutral plasma devices, magnetic confinement plasma devices, reversed field pinch plasma devices, neutral beam injection heating plasma devices, or other high-temperature plasma devices. High-temperature plasma device 16 atomizes ablated sample particles received in ablation plume 14 in a high-temperature plasma and yields ions corresponding to target isotopes of analytical interest and bulk sample matrix components released from ablated sample particles in plasma device 16.

The high-temperature plasma may be generated from a plasma support gas. Plasma support gases include, but are not limited to, e.g., argon (Ar), helium (He), nitrogen ($N_2$), oxygen ($O_2$), air, other support gases, including combinations of these various gases. Support gas pressures in the high-temperature plasma device may be greater than or equal to about 0.5 atm. In some embodiments, support gas pressures in the high-temperature plasma device may be at or above atmospheric pressure.

In some embodiments, high-temperature plasmas may have a temperature above 4,000 Kelvin (K). In some embodiments, high-temperature plasmas may have a temperature between about 5,000 K to about 10,000 K.

Atomized target isotopes may be delivered in a high-temperature plasma plume 18 from high-temperature plasma device 16 into a mass-selective spectrometer 20.

Target isotope ions of analytical importance may be mass-selected in mass spectrometer 20 at selected masses to filter them from the bulk sample matrix components received from high-temperature plasma device 16 in high temperature plasma plume 18 corresponding to original ablated sample 4. Mass-selective spectrometer instruments suitable for use with the present invention include, but are not limited to, e.g., Inductively Coupled Plasma (ICP) devices that are coupled to Mass Spectrometers (ICP-MS), Secondary Ion Mass Spectrometers (SIMS), and Glow Discharge Mass Spectrometers (GD-MS). However, mass spectrometers and mass-selective analyzers are not limited.

Mass-selected target isotope ions and/or tracer isotope ions may be implanted in one or more implant areas 24 of a selected size on the surface of a selected high-purity substrate 22 positioned within mass-selective spectrometer 20 over a selected period of time. Substrate 22 may take the place of a conventional detector in mass spectrometer 20 positioned, e.g., at an ion detection end of spectrometer 20. Mass-selected target isotope ions of analytical importance may be implanted in one or more implant areas 24 on substrate 22 free of bulk matrix components and/or other contaminants present in the original sample. Implanted target isotopes may be pre-concentrated in the localized implant areas 24 on substrate 22. Target isotopes and/or tracer isotopes implanted on substrate 22 may form an isotope dilution standard in the solid phase on substrate 22. Implant areas 24 on high-purity substrate 22 containing implanted target isotopes and tracer isotopes may be of a selected size or area. Size of implant areas is not limited. In a preferred embodiment, implant areas 24 may include a size of less than or equal to about 1 mm or a cross-sectional area less than or equal to about 1 $mm^2$.

Substrate 22 containing implanted target isotopes and/or tracer isotopes may be introduced into an ablation chamber 10 and ablated in an ablation device 2. Implant areas 24 on substrate 22 containing implanted target isotopes of analytical interest and/or tracer isotopes may be ablated with an ablation source 8. Ablation source 8 may be a pulsed UV laser, but the invention is not limited thereto. Target isotopes and tracer isotopes ablated from implant area 24 may be carried in an ablation plume 28 into a high-temperature plasma device 16 where the target isotopes and tracer isotopes may be atomized.

Target isotopes and tracer isotopes atomized in high-temperature plasma device 16 may be introduced in a high-temperature plasma plume 30 into a mass spectrometer 20 where ions may be counted with a mass detector 32. The isotope dilution ratio of both the target isotopes (the unknown isotope) and the tracer isotopes (the known isotope) may then be determined in mass spectrometer 20 free of contaminating elements and interfering sample matrix components. Implantation and pre-concentration of target isotopes and tracer isotopes by the present invention allows ultrasensitive determination of the target isotopes.

Figure 2A:
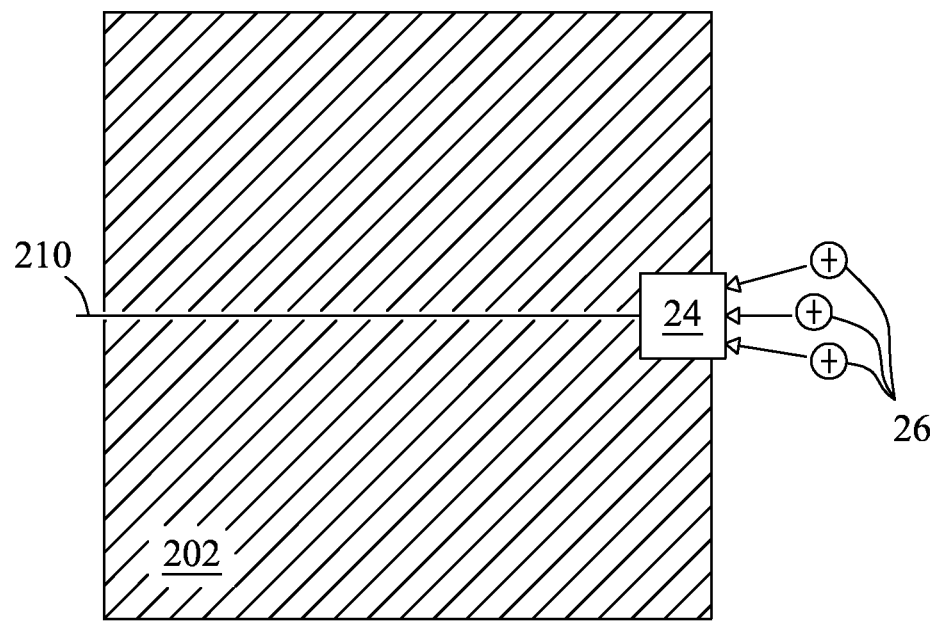
FIGS. 2A-2B illustrate different views of a high-purity substrate for implantation of selected isotopes in concert with the present invention.

FIG. 2A is a schematic illustrating a cross-sectional view of a mounting block 202 to which a high-purity substrate 22 is mounted for implantation of selected isotopes. Substrates 22 may be comprised of high-purity materials including, but not limited to, e.g., silicon, semiconductors, conducting metals, and metal foils. Mounting block 202 may be constructed of an insulating material described further herein in reference to FIG. 3. Substrate 22 may include an implant area 24 of a selected size onto which selected isotopes 26 including, e.g., target isotopes and/or tracer isotopes may be implanted in a mass spectrometer. A bias wire 210 is shown coupled to implant area 24 that applies a negative bias voltage to substrate 22 that polarizes substrate 22 and draws isotopes 26 (e.g., tracer and/or target) from the mass spectrometer to implant area 24.

Figure 2B:
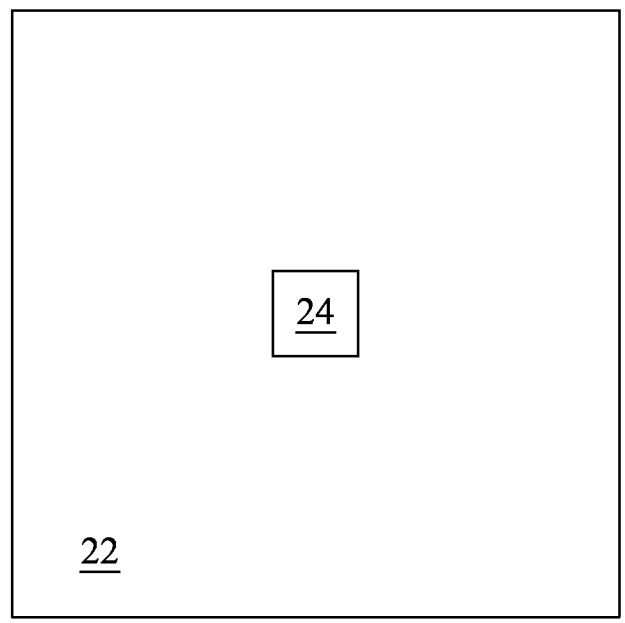

FIG. 2B illustrates a front-face (i.e., implant) view of substrate 22 mounted to mounting block (FIG. 2A). Substrate 22 may include an implant area 24 of a selected cross-sectional area or size for implantation of target isotopes and/or tracer isotopes described previously in reference to FIG. 2A. Implant area 24 pre-concentrates target isotopes for ultrasensitive determination. Best detection limits may be achieved on high-purity substrates that are free of contaminants (e.g., solution derived trace-level elements) and free of bulk sample matrix components that can interfere with the determination of implanted target isotopes of analytical interest. In some embodiments, implant areas 24 may include a cross-sectional area less than or equal to about 1 mm$^2$. However, no limitations are intended.

Holder Assembly

Figure 3:
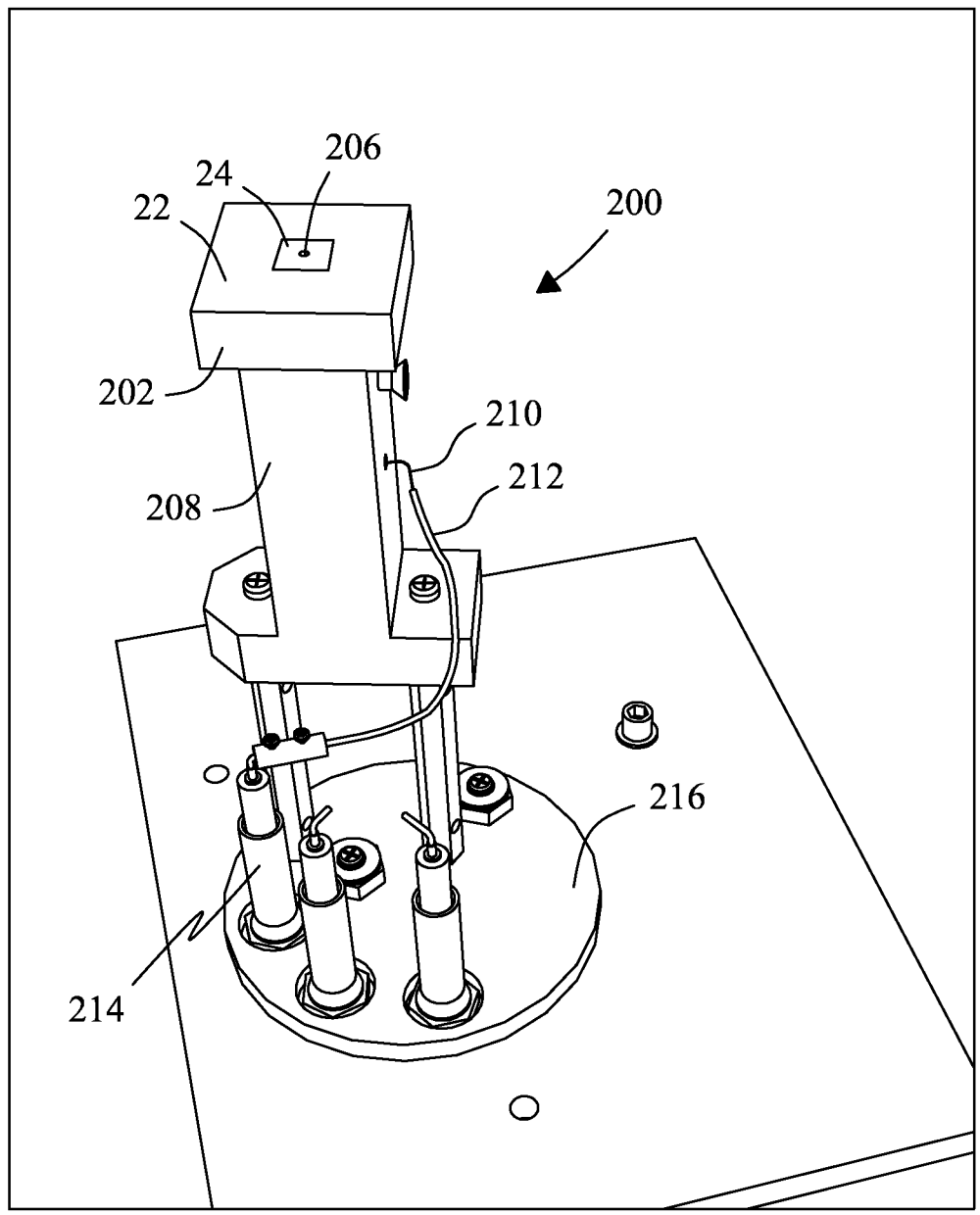
FIG. 3 shows a holder assembly for implantation of selected isotopes in concert with the present invention.

FIG. 3 shows a holder or mount assembly 200 for mounting substrates (termed "micro-implant" substrates) for implantation of target isotopes and tracer isotopes. Target isotopes and tracer isotopes may be implanted in one or more implant areas of a selected size or dimension on the surface of substrate 22, as described previously herein. Holder assembly 200 may include a mounting block 202 constructed, e.g., out of PEEK® (Boedeker Plastics, Shiner, Tex., USA) or another suitable vacuum compatible and electrically insulated material. Mounting block 202 may include a flat-faced surface 204 onto which substrate 22 may be mounted in preparation for implantation of target isotopes and tracer isotopes. Mounting block 202 may include a bias wire 210 (e.g., 0.2 mm wire) comprised of a conducting material such as copper that electrically couples high-purity substrate 22 on mounting block 202 to a high voltage bias source 214. Bias wire 210 may extend from an opening 206 (e.g., a 0.4 mm diameter or another non-limiting dimension) on the surface of mounting block 202 through mount 202 through block support 208. Bias wire 210 may emerge, e.g., from a side of block support 208 and may couple to a coarser (>0.2 mm) wire 212. Wire 212 may then extend from block support 208 and connect with a high voltage source electrically coupled to a high-voltage feed-through 214 positioned on vacuum flange 216, e.g., as shown. In the exemplary embodiment, substrate 22 may be in the form of a metal sheet (e.g., copper foil) 22 that may be soldered to bias wire 212 that emerges through opening 206 on surface 204 of mounting block 202. Bias wire 210 may deliver a selected bias voltage (e.g., negative voltage) to substrate 22 that polarizes the substrate and draws charged target isotope and tracer isotope ions from the mass spectrometer for implantation on the surface of substrate 22 in implant area 24. In various embodiments, substrate 22 may include various high-purity materials described herein including, e.g., a sheet of copper (e.g., copper foil) or another suitable material with selected dimensions (e.g., 0.8 mm×0.4 mm).

Quantity of implanted tracer isotopes and target isotopes is not limited. Quantity of implanted tracer isotopes may be selected based on the ion efficiency of the detection instrument, the pre-concentration factor selected for implanted target isotopes, the ablation time, size of the implant area, the isotopic dilution ratio for both the target and tracer isotopes, and the desired detection limit. Ion efficiency curves detailed further herein may assist the selection of analysis parameters.

Implantation Times

Times selected for implantation (accumulation) of target isotopes and tracer isotopes on the surface of the substrate are not limited. Times may range from minutes to hours or longer. Times selected depend at least in part on the desired level of pre-concentration of target isotopes of interest and desired detection limits for the sample undergoing analysis. In some embodiments, time for implantation may be a minute or longer. In some embodiments, time for implantation may be an hour or longer. In some embodiments, time for implantation may be a day or longer. No limitations are intended.

Ablation Times for Ultrasensitive Determination of Target Isotopes

Ablation times for ablation of implant areas to release implanted target isotopes and tracer isotopes on the surface of the high-purity substrate, e.g., in concert with raster scanning of the surface, are not limited. In some embodiments, ablation may include a raster scan of the implant area that is performed in an ablation time less than or equal to about 80 seconds. In some embodiments, ablation may include a raster scan time of less than or equal to about 60 seconds. In some embodiments, ablation may include a raster scan time of less than or equal to about 50 seconds. In some embodiments, ablation may include a raster scan time of less than or equal to about 40 seconds. In some embodiments, ablation may include a raster scan time of less than or equal to about 30 seconds. In some embodiments, ablation may include a raster scan time of less than or equal to about 20 seconds. In some embodiments, ablation may include a raster scan time of less than or equal to about 10 seconds. Times may be selected that maximize the detector response for released target isotopes and tracer isotopes. However, no limitations are intended.

Isotope Dilution for Determination of Target Isotopes

The present invention includes a new Isotopic Dilution Analysis (IDA) approach for quantitation of target isotopes present in a sample that does not rely on wet chemistry preparation methods. In this approach, a known quantity (or number of ions) of a tracer isotope may be implanted onto the surface of the substrate along with target isotopes of analytical interest obtained from a sample. Tracer isotopes are selected that assist the determination of the concentration of a target isotope of interest in the original sample, as described herein. Implantation of both isotopes generates an isotope dilution standard in the solid phase on the surface of the substrate. Ablation of the implant area containing the tracer isotope and the target isotope of interest generates a signal response for both the tracer isotope and the target isotope in a mass spectrometer. Detector response (e.g., in ion counts per second) for the tracer isotopes in the mass spectrometer permits the concentration of the target isotope of interest in the original sample to be determined at a detection limit significantly lower than previously attained. For example, peak height (detector response) of the ion current signal for the tracer isotope corresponds to a known quantity of implanted tracer isotope ions, which may then be used to calculate the number of ions corresponding to the respective detector response (peak height) of the target isotope of interest. Number of ions for the target isotope then permits the concentration of target isotopes in the original sample to be determined. Tracer isotopes may be isotopes of the same element as the target isotope or isotopes from different elements. For example, tracer isotopes may include: 1) a different isotope of the target isotope when the target isotope has multiple different isotopes; and 2) isotopes of a different element when the target isotope is a mono-isotopic element. A different isotope of the same element is a preferred tracer isotope given the expected close mass separation and nearly identical or similar chemical properties. An isotope of a different element may also be used as a tracer isotope.

Tracer Isotopes

Tracer isotopes are preferred that include a mass separation of ±5 mass units and similar chemical properties as the target isotopes of analytical interest. Isotopes suitable for use as tracer isotopes when the target element is not mono-isotopic include, but are not limited to, e.g., Mg-25 or Mg-26 for Mg-24; K-41 for K-39; Ca-44 for Ca-40; Ti-46, Ti-47, Ti-49, or Ti-50 for Ti-48; V-50 for V-51; Cr-50, Cr-53, or Cr-54 for Cr-52; Fe-54, Fe-57, or Fe-58 for Fe-56, and like isotopes.

In some embodiments, tracer isotopes may be implanted in the mass spectrometer on the surface of the substrate in the same implant area as the target isotope of interest, e.g., so that an identical background signal is obtained. In some embodiments, tracer isotopes may be implanted on a different implant area on the substrate than the target isotopes of interest. In yet other embodiments, a different isotope of the same element or an isotope of an analogous element different from the target isotope with an identical mass may be implanted. Implantation of tracer isotopes on the substrate in the mass-selective spectrometer may be performed before or after implantation of the target isotopes. No limitations are intended.

Response Profiles for Determination of Target Isotopes

Figure 4:
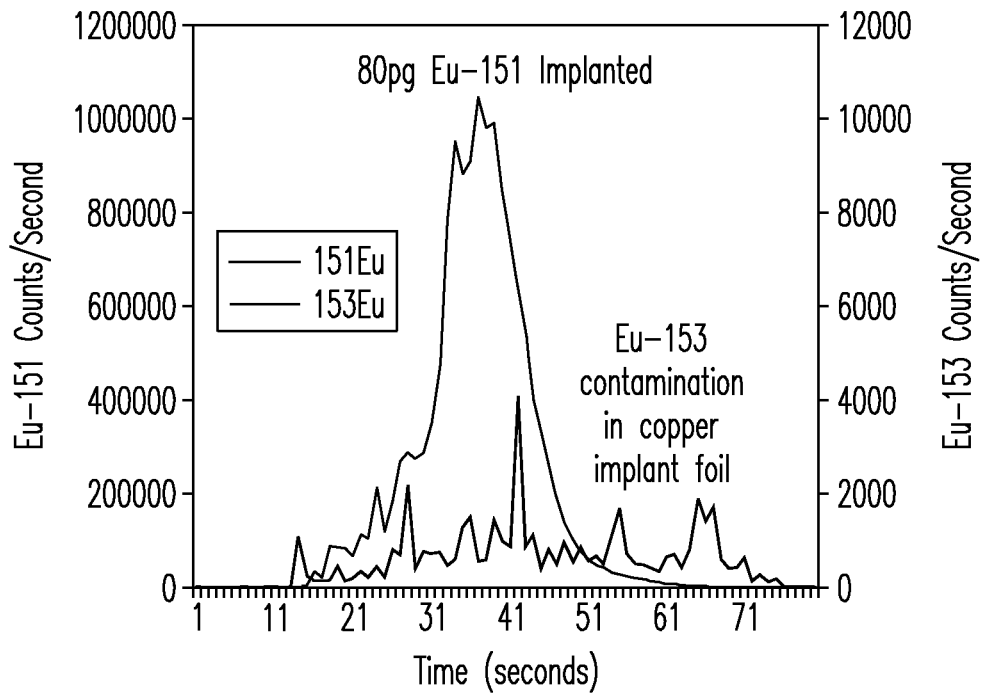
FIG. 4 shows an ion response profile for an exemplary trace-level target isotope implanted and determined in accordance with the present invention.

FIG. 4 shows ion response profiles for a representative tracer isotope (e.g., Eu-151) implanted onto a copper foil substrate at a level of 80 picograms (pg) ($80 \times 10^{-12}$ g) and a representative target isotope (Eu-153) present in the copper foil at a natural abundance. Isotopes were determined in a mass spectrometer in accordance with the present invention. In the figure, the ion current response (in counts per second) for both the target isotope and the tracer isotope is plotted as a function of time. The isotope dilution ratio may be calculated based on the detector responses of the two isotopes (i.e., the ratio of the detector response values). Then, because the quantity of tracer isotope is known, the response for the target Eu-153 isotope may be correlated to a concentration of the target isotope in the sample.

Figure 5:
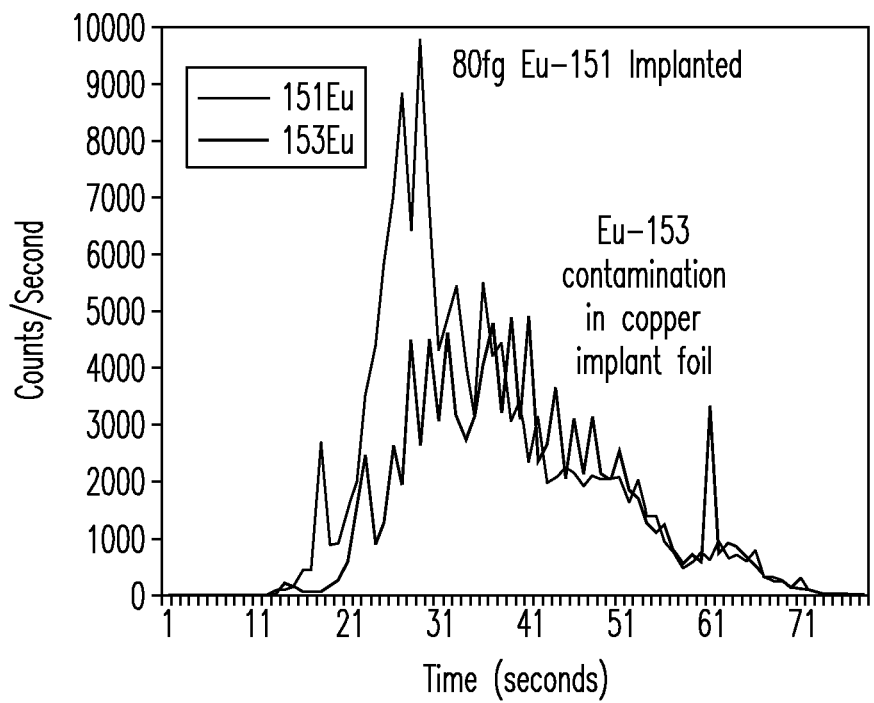
FIG. 5 shows an ion response profile for an exemplary trace-level target isotope implanted and determined in accordance with the present invention.

FIG. 5 shows an ion response profile for a trace-level target isotope (e.g., Eu-153) of analytical interest present at a natural abundance in a copper foil (substrate) and a representative tracer isotope (e.g., Eu-151) implanted onto the substrate at a level of 80 femtograms (fg) ($80 \times 10^{-15}$ g) (or $3.19 \times 10^8$ atoms of Eu-151). Quantity of implanted tracer isotope is at a level 1000 times lower than that previously described in reference to FIG. 4. Results show the present invention can selectively implant and pre-concentrate trace-level quantities of specific isotopes at specific locations on a substrate for subsequent detection at high-signal-to-background ratios greater than about 10 to less than about 100. Results of the instant example show a detection limit in the attogram ($10^{-18}$ g) range (or $10^6$ atoms/cm$^2$) or lower can be obtained. However, as will be appreciated by those of ordinary skill in the art, substrates with a lower level of trace element contamination or no trace element contamination such as silicon substrates can permit implantation of yet lower concentrations of tracer isotopes e.g., 0.8 fg of Eu-151 (or $3.19 \times 10^6$ atoms) that still yield a detectable signal suitable for determining concentrations of selected target isotopes of interest. The present invention is not intended to be limited to the exemplary target isotopes described here. All isotopes as will be selected by those of ordinary skill in the art in view of the disclosure are within the scope of the present invention.

Figure 6:
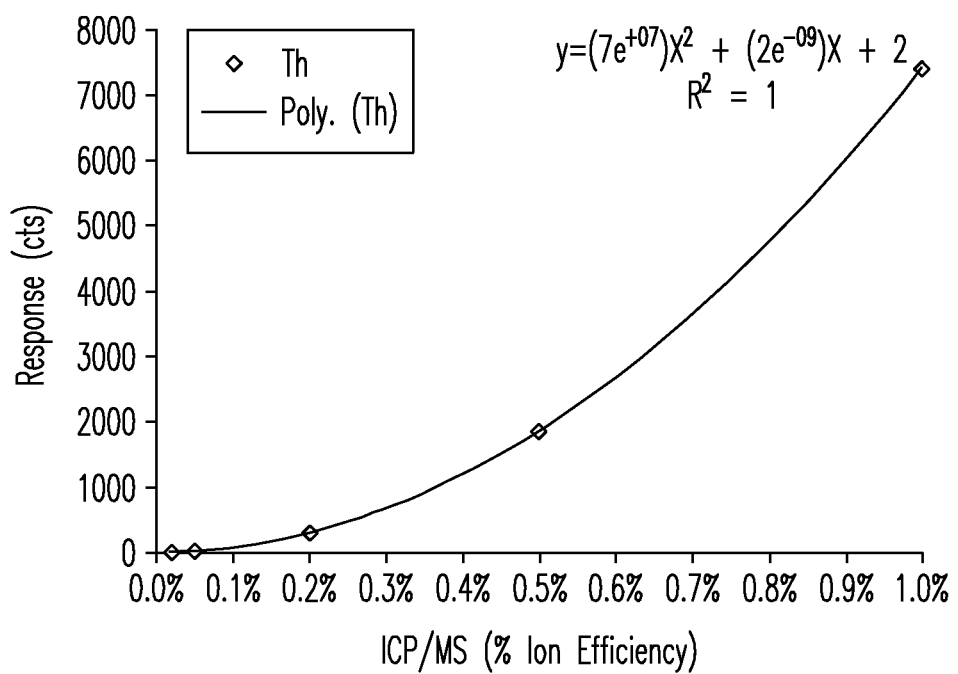
FIG. 6 plots the ion detector efficiency for an exemplary isotope implanted and determined in an ICP/MS system in accordance with the present invention.

FIG. 6 plots the ion response for an exemplary thorium isotope as a function of the ion detector (i.e., ICP/MS) efficiency. Results show the ion detector efficiency affects the number of ion counts obtained for implanted isotopes of analytical interest. Detector efficiency also affects the quantity of isotopes that must be implanted onto the surface of the substrate to obtain a suitable or desired detection limit for the isotopes of analytical interest. For example, the regression shows that at a detection efficiency of 1%, the ion response is 7000 times greater than that observed for an instrument with a detector efficiency below 0.1%.

Detection Limit for Ultrasensitive Determination of Target Isotopes

The present invention provides ultrasensitive determination of the concentration of target isotopes. In some embodiments, the present invention determines the concentration of target isotopes at a detection limit of at least about $10^8$ atoms per cm$^2$ or lower. In some embodiments, the present invention determines the concentration of target isotopes at a detection limit of at least about $10^7$ atoms per $cm^2$ (2 ppt) or lower. Ultrasensitive determination of target isotopes stems in part from removing or minimizing quantity of bulk sample matrix components that can swamp the detector, and removing common sources of contamination including, e.g., from wet chemistry reagents used to prepare conventional samples for analysis including, but not limited to, e.g., dissolution acids, other reagents, as well as contaminants leached from containers. Various factors influence detection limits including, e.g., ion implantation efficiency in the mass spectrometer; size of the implant areas on the surface of the substrate, where smaller implant areas enhance pre-concentration of the target isotopes (i.e., so-called pre-concentration factor); time allowed for implantation, which affects loading or concentration of target isotopes on the substrate; laser ablation efficiency during analysis of target isotopes and/or tracer isotopes; ablation times, where shorter ablation times yield better discrimination values against background; and backgrounds stemming from isotope impurities on the implanted substrate. Enhanced detection limits obtained in concert with the present invention are due in part to the elimination or minimization of surface contaminants stemming from such sources as liquid dissolution reagents, leaching and introduction of contaminants from containers, or other contamination sources that normally interfere with quantitation of target isotopes of interest.

EXAMPLES

The following examples provide a further understanding of various aspects of the present invention.

Example 1

Isotopic Dilution (1)

Implantation of Both Target Isotopes and Tracer Isotopes

In one isotope dilution approach of the present invention for analysis of solids, a known quantity of a selected tracer isotope may be implanted in one or more selected implantation areas on the surface of a high-purity substrate free of contaminants or other impurities before or after implantation of a target isotope. Implantation of both the tracer isotope and the target isotope forms an isotopic dilution standard on the surface of the substrate in the solid state substantially free of contaminants or other impurities that can interfere with determination of the target isotopes. Ablation of the implantation area containing both the tracer isotope and the target isotope permits determination of the isotopic ratio of both isotopes in a mass spectrometer at a detection limit of at least about $10^7$ atoms per $cm^2$ (2 ppt) or lower which permits ultrasensitive determination of the concentration of the target isotope in the sample.

Example 2

Isotopic Dilution (2)

Target Isotopes on a Substrate Composed of Tracer Isotope

In another isotope dilution approach of the present invention, substrates on which target isotopes are implanted may be composed of the tracer isotope selected for determination of the target isotope of interest. In this approach, only the target isotope of analytical interest is implanted in one or more implantation areas on the surface of the substrate free of contaminants or other impurities. When implanted on the substrate, the target isotope forms an isotope dilution standard with the substrate in the solid state free of contaminants or other impurities that can interfere with determination of the target isotopes. Ablation of the implant area containing both the target isotope of analytical interest and the known quantity of tracer isotopes permits determination of the isotopic ratio of both isotopes in a mass spectrometer at a detection limit of at least about $10^7$ atoms per $cm^2$ (2 ppt) or lower which permits ultrasensitive determination of the concentration of the target isotope in the sample.

Example 3

Implantation of Exemplary Eu-151 Tracer Isotope

The system of FIG. 1 was used. An implantation substrate composed of copper foil (e.g., 0.8 mm×0.4 mm) was mounted onto a holder assembly (FIG. 3). The holder assembly was introduced into a ICP-MS instrument system. A 1 ppm solution of Europium (Eu) containing a natural distribution of Eu isotopes was aspirated through the plasma into the MS. The quadrupole mass filter of the mass spectrometer was set to the mass for Eu-151 used as the tracer isotope and implanted. An ion current (conductivity) of 15 pA was measured from the copper implant. A negative bias (−1500 V) was then applied to the micro-implant foil (substrate) to increase the positive ion current. Eu-151 ions were implanted for a period of 56 minutes to yield an estimated implantation quantity of at least 80 pg of Eu-151 on the micro-implant foil. The holder assembly was then removed from the vacuum system and the implant foil was mounted via double-sided tape onto a larger piece of copper foil and placed into a laser ablation cell coupled to the ICP-MS. Laser ablation parameters were selected including an implant area size of 780 μm, a raster scan speed of 30 μm/sec, an ablation power of 6 Joules/cm$^2$, a repetition rate of 10 Hz, and an acquisition time of 80 sec. FIG. 4 shows the ion response of the target (i.e., Eu-151) isotope ablated from the implanted copper foil substrate.

Example 4

Implantation of Exemplary Eu-151 Tracer Isotope

The experiment of EXAMPLE 1 was repeated. Concentration of the Eu-containing solution was reduced 1000-fold to 1 ppb and the Eu-151 tracer isotope was again implanted onto a copper foil substrate using an identical implantation period to reduce the expected concentration of Eu-151 on the substrate from 80 picograms (pg) to 80 femtograms (fg) ($3.19×10^8$ atoms of Eu-151). The sample holder was then removed from the vacuum system and the implant foil was mounted via double-sided tape onto a larger piece of copper foil and placed into the laser ablation cell. The laser ablation system was coupled to an ICP-MS. The laser ablation system was coupled to an ICP-MS. Laser ablation parameters included an implant area size of 780 μm, a raster scan speed of 30 μm/sec, an ablation power of 6 Joules/cm$^2$, a repetition rate of 10 Hz, and an acquisition time of 80 sec. FIG. 5 plots the ion response of the Eu-151 tracer isotope ablated from the Eu-151 micro-implanted substrate. Results show the 80 fg of implanted Eu-151 on the copper foil is readily detectable despite trace amounts of naturally occurring Eu-151 being present in the copper foil. Differences in the signal profile between Eu-151 (implanted+natural) and Eu-153 (natural) is very distinctive, as no other rare-earth elements directly overlap the Eu isotopes.

Example 5

Implantation of Trace-Level concentrations of U-238 and Th-232

A ~5 g sample of polytetrafluoroethylene (PTFE), a synthetic fluoropolymer of tetrafluoroethylene (DuPont, Wilmington, Del., USA) was chemically analyzed by a conventional method to determine concentrations of trace-level target isotopes of Thorium (Th-232) and Uranium (U-238) in the sample. TABLE 1 lists results from the conventional chemical analysis.

TABLE 1

Results from conventional chemical analysis of PTFE.

| Isotope | Isotope | pg/g | Atoms/g | T(1/2)year | Lambda | uBq/kg |
|---|---|---|---|---|---|---|
| Th | 232 | 6.055 | 1.57E+10 | 1.40E+10 | 1.57E−18 | 25 |
| U | 238 | 58.40 | 1.48E+11 | 4.50E+09 | 4.88E−18 | 722 |

The PTFE sample was also analyzed in accordance with the present invention. The system of FIG. 1 was used. The sample was twice ablated to determine the amount of material removed in one hour. TABLE 2 lists data from a bottom raster (single pass ablation) scan of the implantation substrate. TABLE 3 lists data from a top raster (double pass) scan of the implantation substrate.

TABLE 2

Mass of sample ablated by Laser Ablation
Laser Ablation Parameters: (Single Pass)

| raster ablation area (4 × 5 mm) | 20 | $mm^2$ |
|---|---|---|
| laser implant area size | 350 | um |
| laser spacing | 375 | um |
| Pulse rate | 10 | Hz |
| laser power | 100 | % |
| Total Time | 41 | minutes |
| Laser Ablation of Plastic: (First Raster) | 0.00107 | grams/hour |
| Starting weight | 1.00637 | grams |
| Weight after ablation | 1.00564 | grams |
| Ablation weight | 0.00073 | grams |

TABLE 3

Mass of sample removed by Laser Ablation
Laser Ablation Parameters: (Double Pass)

| raster ablation area (4 × 5 mm) | 20 | $mm^2$ |
|---|---|---|
| laser implant area size | 350 | um |
| laser spacing | 375 | um |
| Pulse rate | 10 | Hz |
| laser power | 100 | % |
| Total Time | 82 | minutes |
| Laser Ablation of Plastic: (Second Raster) | 0.001288 | grams/hour |
| Starting weight | 1.00564 | grams |
| Weight after ablation | 1.00388 | grams |
| Ablation weight | 0.00176 | grams |

Average amount of PTFE material removed by ablation was about 0.001178 grams of PTFE per hour, corresponding to $7.41 \times 10^5$ atoms of Th-232 and $6.96 \times 10^6$ atoms of U-238 implanted from the sample into a small (1 $mm^2$) implant area on a suitable low background substrate material such as ultra-pure copper metal. TABLE 4 lists data from the determination analysis.

TABLE 4

Mass of sample ablated and atoms implanted in 4 hours

| Ion Efficiency Implant Analysis | | grams per/hr. | Ablation Hours | grams Sample | Isotope | Atoms Implant |
|---|---|---|---|---|---|---|
| 1.0% | 1.0% | 0.001178 | 4.0 | 0.004712 | Th-232 | 7.41E05 |
| | | | | | U-238 | 6.96E06 |

Following implantation of the target thorium isotope Th-232 and the tracer isotope U-238, the implant substrate was removed and placed in a laser ablation cell and ablated using a 10 second line raster. The 10-second ablation window produces a total of about 7,407 counts of Th-232 and about 69,642 total counts of U-238 using a 1% ion efficiency mass spectrometer. FIG. 6 plots the ion efficiency for detection of the target isotope Th-232. Results indicate that background count rates are less than about 1 count per second and generate less than about 10 total counts over the 10 second analysis period.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

What is claimed is:

1. A method for ultrasensitive determination of a target isotope in a sample, the method comprising the steps of:
    mass-selecting ions of the target isotope in a mass-selective spectrometer introduced from a high-temperature plasma source to isolate the target isotope from sample matrix components and/or contaminants present in the sample;
    implanting the isolated target isotope onto the surface of a high-purity substrate in an implant area of a selected size to pre-concentrate the target isotope thereon free of sample matrix components and/or contaminants;
    implanting a known quantity of a tracer isotope in the implant area on the substrate to obtain a ratio of the target isotope and the tracer isotope in the solid state that defines an isotope dilution standard thereon;
    ablating the implant area containing the target isotope and the tracer isotope; and
    determining the concentration of the target isotope at a detection limit of at least about $10^8$ atoms per $cm^2$ or lower.

2. The method of claim 1, wherein determining the concentration of the target isotope includes a detection limit of at least about $10^7$ atoms per $cm^2$ (2 ppt) or lower.

3. The method of claim 1, wherein determining the concentration of the target isotope includes determining the isotope dilution ratio based on the ion detector response of both the tracer isotope and the target isotope.

4. The method of claim 1, wherein the method alternatively includes implanting the target isotope on a high-purity substrate comprising the selected tracer isotope to form an isotope dilution standard in the solid phase on the surface of the substrate.

5. The method of claim 1, further including ionizing a sample containing the target isotope in a high-temperature plasma source prior to implanting the target isotope.

6. The method of claim 1, wherein the high-purity substrate replaces a mass detector in the mass-selective spectrometer.

7. The method of claim 1, wherein the tracer isotope is implanted in the implant area on the surface of the substrate before or after the target isotope of interest.

8. The method of claim 1, wherein the tracer isotope is either a surrogate isotope of a different element having a mass identical to or adjacent to that of the target isotope, or a different isotope of the same element as the target isotope.

9. The method of claim 1, wherein the implant area on the surface of the high-purity substrate includes a size of less than or equal to about 1 mm.

10. The method of claim 1, wherein the target isotope is pre-concentrated on the surface of the substrate by a factor of at least about 10 times or greater.

11. The method of claim 1, wherein ablation of the implant area containing the pre-concentrated target isotope and the tracer isotope is performed in a time of less than or equal to about 30 seconds on average; or a time of less than or equal to about 10 seconds on average.

12. The method of claim 1, wherein implantation of the tracer isotope is performed in the same mass spectrometer that determines the concentration of the target isotope.

13. The method of claim 1, wherein the implantation of the tracer isotope is performed in a mass spectrometer different from the mass spectrometer that determines the concentration of the target isotope.

14. A substrate, comprising:
a target isotope from an ionized sample and a known quantity of a tracer isotope implanted from a high temperature plasma plume in an implant area of a selected size that form an isotope dilution standard in the solid phase on the surface of the substrate substantially free of bulk sample matrix components and/or solution contaminants, the implant area containing the implanted isotopes upon analysis in a mass spectrometer determines the concentration of the target isotope at a detection limit of at least about $10^8$ atoms per $cm^2$ or lower.

15. The substrate of claim 14, wherein the detection limit for the target isotope is at least about $10^7$ atoms per $cm^2$ or lower.

16. The substrate of claim 14, wherein the determination of the implant area the determination of the concentration of the target isotope in the sample at a detection limit of at least about $10^7$ atoms per $cm^2$ (2 ppt) or lower.

17. The substrate of claim 14, wherein the tracer isotope is either a surrogate isotope of a different element having a mass identical to or adjacent to that of the target isotope, or a different isotope of the same element as the target isotope.

18. The substrate of claim 14, wherein the target isotope is pre-concentrated in the implant area on the surface of the substrate by a factor of about 10 times or greater.

19. The substrate of claim 14, wherein the implant area on the surface of the substrate includes an area less than or equal to about 1 $mm^2$ on average.

* * * * *